(12) United States Patent
Nalin

(10) Patent No.: US 7,704,235 B2
(45) Date of Patent: Apr. 27, 2010

(54) SYSTEM AND DEVICE FOR MEDICALLY TREATING AN INDIVIDUAL

(76) Inventor: David R. Nalin, 100 Lucky Hill Rd., West Chester, PA (US) 19382

( * ) Notice: Subject to any disclaimer, the term of this patent is extended or adjusted under 35 U.S.C. 154(b) by 0 days.

(21) Appl. No.: 12/288,905

(22) Filed: Oct. 24, 2008

(65) Prior Publication Data
US 2009/0131847 A1    May 21, 2009

Related U.S. Application Data

(62) Division of application No. 11/507,876, filed on Aug. 22, 2006, now Pat. No. 7,637,895.

(51) Int. Cl.
*A61M 5/00* (2006.01)
(52) U.S. Cl. ..................................... 604/187
(58) Field of Classification Search .................. 604/187, 604/190, 191, 4.01, 181, 182, 218, 6.15
See application file for complete search history.

(56) References Cited

U.S. PATENT DOCUMENTS 3,960,139 A * 6/1976 Bailey ........................ 600/575
5,039,401 A * 8/1991 Columbus et al. ........... 210/117
5,064,418 A * 11/1991 Cronin ........................ 604/190
6,623,472 B1 * 9/2003 Reincke et al. .............. 604/522

* cited by examiner

*Primary Examiner*—Nicholas D Lucchesi
*Assistant Examiner*—Brooke M Matney
(74) *Attorney, Agent, or Firm*—James Ray & Assoc

(57) ABSTRACT

A system for medically treating/vaccinating an individual comprising a first syringe, containing an anticoagulant material therein, for drawing a sample of blood from the individual. A centrifuge is provided for centrifuging the sample of blood contained within the first syringe to obtain a buffy coat. A second syringe comprising a second plunger and at least one microtubule member containing one of a treatment agent and a vaccine antigen. At least one open end formed within the at least one microtubule member for drawing a portion of the buffy coat therein and exposing the buffy coat to one of the treatment agent and vaccine antigen. A second needle capable of being attached onto the second syringe for introducing the exposed sample into the individual to effect treatment/vaccination thereof. This system is capable of allowing a plurality of treatment agents and/or vaccine antigens to be simultaneously applied to an individual.

16 Claims, 2 Drawing Sheets

ND DEVICE FOR MEDICALLY
SYSTEM AND DEVICE FOR MEDICALLY TREATING AN INDIVIDUAL

CROSS-REFERENCES TO RELATED APPLICATIONS

This application is a Divisional Application of a prior non provisional application Ser. No. 11/507,876 filed Aug. 22, 2006, now issued as U.S. Pat. No. 7,637,895 on Dec. 29, 2009. This application is also closely related to co-pending application Ser. No. 11/478,070, filed Jun. 29, 2006 entitled "A Method of Medically Treating An Individual".

FIELD OF THE INVENTION

The invention relates, in general, to a system and device to medically treat and/or immunize an individual and, more specifically, to a system and device for using an immunogenic antigen exposed blood sample to medically treat and/or immunize an individual.

BACKGROUND OF THE INVENTION

Immunization of individuals has long been a known technique for controlling diseases such as measles, mumps, rubella, polio, hepatitis and, more recently, chicken pox. Conventional immunizations deliver either an attenuated live strain of a pathogen or a killed organism or an immunogenic antigen derived from the targeted pathogen or its products, or one produced using recombinant genetic technology. Classical immunization delivers the vaccine by injection or by the enteric route. This approach is very indirect, requiring the antigen to be taken up by immunocytes before or after dispersion from the injection site to the surrounding tissue. The immunocytes then migrate to lymphatic nodes or the spleen where antigen processing continues, or, for live vaccines, where the attenuated vaccine strain organisms multiply and are disseminated from. Exposure of immunocytes to the antigens or the attenuated pathogens triggers humoral and cellular mediated immune responses, which lead to absorption of antigens or elimination of attenuants followed by long lasting protection from disease caused by the respective pathogen(s).

The enteric route requires that the antigen or organism survive the numerous barriers posed by the gastric acid, digestive enzymes, competing microorganisms and biologically active lumenal or tissue substances, to reach a site from which the antigen or attenuated organism or products derived from an organism can be absorbed and can stimulate the immune system inducing a protective response. Other approaches, such as anti-idiotype immunization, or DNA injection, have been proposed but have not yet proven efficacious or safe in humans.

The routes of immunization for conventional vaccines have been parenteral (intramuscular, subcutaneous or intradermal) or oral/enteric. Evidence exists that other routes (rectal, aerosol/nasal, dermal, etc.) could be used, but various practical and safety limitations have blocked widespread applications via these routes. Direct administration of vaccines via the intravenous route has been avoided due to the possible risk of severe systemic allergies (anaphylaxis) in sensitive individuals, or the risk of embolization of vaccine components or of air.

In any case, all routes to date are modeled on the existing concept of multiple vaccinations, using individual (monovalent) or combination (polyvalent) vaccines. A reduction in the total doses needed for parenteral vaccines has been limited by the lack of lasting immune responses after only one dose of some vaccines, by interference between antigens when combined, and sometimes by safety or stability issues.

The expense of and barriers to vaccination are aggravated not only by the growing number of vaccines, doses, clinic visits for vaccinations, etc., but the need to manufacture multiple formulations free from adventitious organisms, noxious ingredients and/or contaminants or impurities. Additionally, the necessity of cold chain maintenance for many vaccines raises another barrier against vaccination in remote and impoverished areas. Also, relatively large volumes and large doses of most current vaccines are needed to ensure that some of the vaccine is injected into areas where it will come into contact with immunocytes within tissue, and to generate responses of protective magnitude.

Due to the increasing number of vaccines being introduced for disease control, an additional series of problems have arisen with the use of conventional vaccines. These problems include:

(a) Excessive expense for the vaccine products, vaccine administration, storage and clinic/office visits.

(b) Problems of compliance with costly and complex vaccination schedules.

(c) Unavailability of certain vaccines in impoverished areas.

(d) Growing dependence on health care workers for delivery of the vaccines.

(e) Lack of health care workers in many areas.

(f) Multiplicity of injections with complex schedules and injection site discomfort.

(g) Interference between certain antigens in polyvalent vaccines.

(h) Age restrictions for some vaccines.

(i) Production and supply limitations with frequent shortages.

(j) Safety concerns.

In view of the multiplicity of concerns associated with the administration of conventional vaccines, there is a need in the art for a new and revolutionary system and device for immunizing individuals, both humans and animals, which mitigates the problems enumerated above. There is also a need in the art for a new and revolutionary system and device for medically treating individuals, which would effectively deliver various types of treatment material throughout an individual's body.

OBJECTS OF THE INVENTION

It is therefore an object of the invention to provide a system and a device for immunization that minimizes the amount of antigen, attenuant or other immunogen needed and the number of doses and clinic visits required, while making possible polyvalent simultaneous immunizations.

It is a further object of the invention to provide a system and device for immunization that reduces the costs of immunization by reducing dose quantity, number of doses needed, number of visits needed, and cold chain dependence of the vaccine.

It is another object of the invention to provide a system and a device for immunization that is capable of using whole blood or buffy coat cells.

It is a further object of the invention to provide a system and a device for the delivery of materials, in addition to antigens, or attenuants, throughout an individual's body such as therapeutic drugs, virus vectors, genes, DNA, RNA, isotopes, and other therapeutic substances.

It is yet another object of the invention to provide a system and a device to facilitate the treatment of AIDS and other infectious disorders.

In addition to the various objects and advantages of the invention which have been described in some specific detail above it should be noted that various other objects and advantages of the present invention will become more readily apparent to those persons who are skilled in the relevant art from the following more detailed description, particularly, when such description is taken in conjunction with the attached drawing Figures and with the appended claims.

SUMMARY OF THE INVENTION

Briefly, and in accordance with the forgoing objectives, the invention comprises a system for medically treating/vaccinating an individual. This system comprises a first syringe for drawing a sample of blood from the individual. The first syringe comprises a first needle, a first plunger, and a tubular member extending between the first needle and the first plunger. This tubular member contains an anticoagulant therein. A centrifuge means for centrifuging the sample of blood contained within the first syringe to obtain a buffy coat and to enable one to express the packed red blood cell layer or alternatively, the plasma layer to expose the buffy coat at the syringe orifice by means of a dual aperture (capped) syringe, or by centrifuging the syringe with the orifice side up. A second syringe comprising a second plunger and at least one microtubule member containing one of a treatment agent and a vaccine antigen. At least one open end formed within the at least one microtubule member for drawing a portion of the buffy coat therein and exposing the buffy coat to one of the treatment agent and vaccine antigen. A second needle capable of being attached onto the at least one open end of the at least one microtubule member for introducing the exposed sample into the individual to effect treatment/vaccination thereof.

DETAILED DESCRIPTION OF THE INVENTION

Figure 2:
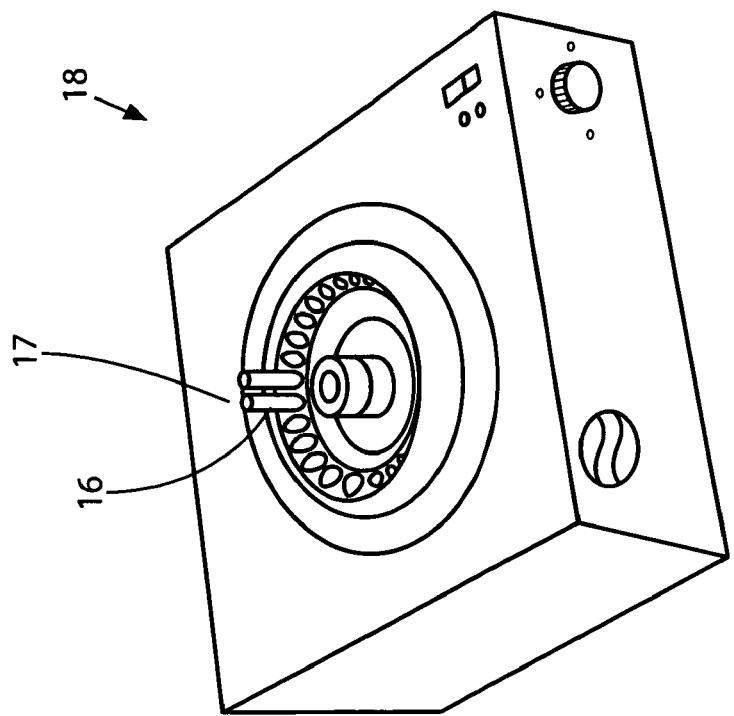
FIG. 2 shows a centrifuge means for centrifuging the sample of blood contained within the first syringe to obtain a buffy coat.

Prior to proceeding to a more detailed description of the invention, it should be noted that identical components having identical functions have been designated with identical reference numerals for the sake of clarity.

Figure 1:
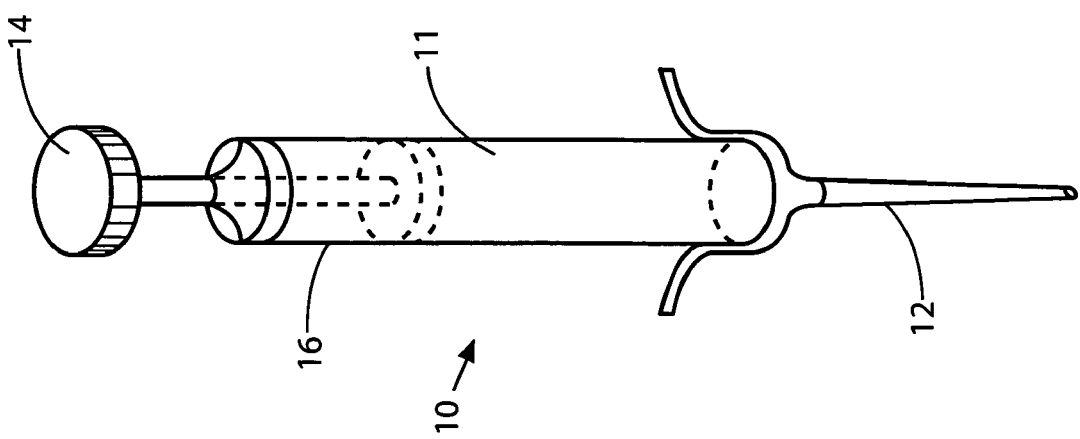
FIG. 1 shows a first syringe for drawing a sample of blood from an individual.
Figure 4:
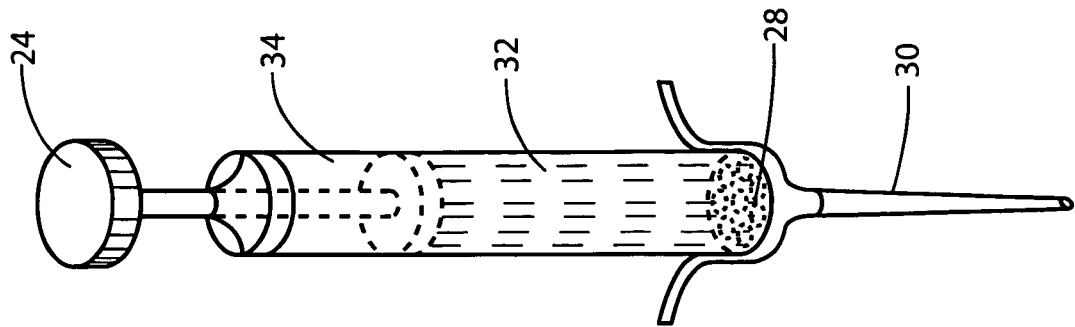
FIG. 4 shows the second syringe with an attachable needle for re-injection of the exposed sample of FIG. 3 into an individual.

Reference is now made to FIG. 1, which shows a first syringe, generally indicated as 10, for drawing a sample of blood 11 from the individual. The first syringe 10 comprises a first needle 12, a first plunger 14, and a tubular member 16 extending between the first needle 12 and the first plunger 14. An anticoagulant material is contained within the tubular member 16 of the first syringe 10.

As illustrated in FIG. 2, a centrifuge means, generally indicated as 18, may be provided for centrifuging the sample of blood contained within the first syringe 16 to obtain a buffy coat or white blood cells 20 from the sample of blood. A cap 17 may be used to cap the first syringe 16 during centrifugation. Any well-known centrifuge device may be used for centrifuging the sample of blood. After centrifugation of the blood-filled syringe (with the aperture end up and removal of the cap), the plasma is pushed out until the buffy coat alone is present, beginning at the distal syringe aperture. The dimensions of the syringe aperture(s) and the antigen or treatment microtubule aperture must provide precise docking of the two syringe devices.

Figure 3:
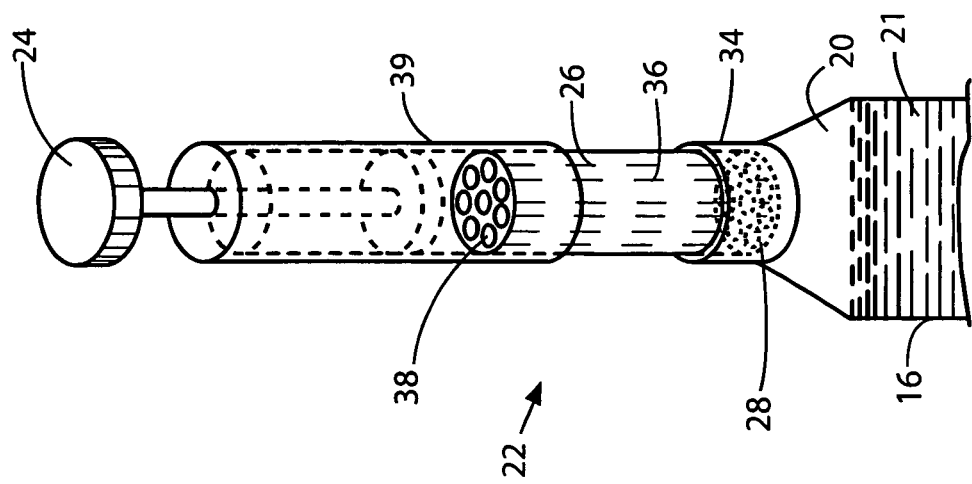
FIG. 3 shows the second syringe, including a plurality of microtubules, for withdrawing one of a buffy coat sample or a whole blood sample and exposing the sample to antigen or treatment material.

After centrifugation, as shown in FIG. 3, the tubular member 16 of the first syringe 10 shows an example wherein the first syringe 10 is centrifuged with the outlet aperture up so that the buffy coat 20 is above the packed red blood cells 21. If the tubular member 16 is centrifuged with the outlet aperture down (capped), red blood cells will be the bottom layer, below the buffy coat, and will be expressed to bring the buffy coat to the aperture. A second syringe, generally indicated as 22, comprises a second plunger 24, which may be built into the syringe, and at least one microtubule member 26 containing one of a treatment agent and a vaccine antigen. At least one open end 28 is formed within the at least one microtubule member 26 for drawing a portion of the buffy coat 20 therein and exposing the buffy coat 20 to one of the treatment agent and vaccine antigen. A second needle 30 is provided which is capable of being attached onto the at least one open end 28 of the at least one microtubule member 26 for introducing the exposed sample 32 into the individual to effect treatment/vaccination thereof.

The use of the centrifuge means 18 is optional as the system of the present invention does rot require that the sample of blood be centrifuged in order to obtain the buffy coat layer. A portion of the whole blood sample obtained from the individual may be directly exposed to the antigen or treatment material within the second syringe 22.

The first plunger 14 and the first needle 12 are capable of being removed from the tubular member 16 so that the tubular member 16 may be placed directly into the centrifuge means 18 or stored for future use. Also, since the first plunger 14 and/or the first needle 12 can be removed from the tubular member 16, the buffy coat or the whole blood sample may be directly removed from this tubular member 16 with the second syringe 22.

At least one cap 17 may be provided for sealing the tubular member 16 to enable the tubular member 16 to be placed within the centrifuge means 18 and/or a storage device.

The first syringe 10 can also include means to expel red blood cells from within the tubular member 16 after subjecting the sample of blood 11 to the centrifuge means 18. This means to expel red blood cells can comprises the original first needle 12 which was removed to allow the sample to be centrifuged, another attachable needle, or any other well known means.

As stated above, a second syringe 22 comprises a second plunger 24 and at least one microtubule member 26 containing one of a treatment agent and a vaccine antigen. At least one open end 28 is formed within the at least one microtubule member 26 for drawing a portion of the buffy coat 20 therein and exposing the buffy coat 20 to one of the treatment agent and vaccine antigen. This second plunger 24 is capable of fitting loosely on the at least one microtubule 26 to prevent an airlock on the at least one microtubule 26 while drawing the buffy coat 20 therein. This design would allow the buffy coat 20 to be drawn into the at least one microtubule 26 by means of capillary action. Alternatively, the second plunger 24 may be tightened to create an airlock and the buffy coat 20 may be drawn into the at least one microtubule 26 by means of syringe plunger pressure applied from the second plunger 24. It is also necessary for the second plunger 24 to be tightened to create an airlock so that the exposed sample may be introduced into the individual. The second plunger 24 is sterile and has a volume that exceeds the dead space of the second needle 30 and the at least one microtubule 26.

As many as eight or more microtubules 26 may be provided in the second syringe 22. Each of these microtubules 26 may be pre-coated with a different vaccine antigen or treatment material so that the individual's sample of blood is capable of being simultaneously exposed to a plurality of these treatment agents and/or vaccine antigens. The plurality of microtubules can be formed according to two embodiments. In the preferred embodiment, the second syringe 22 can include a cylindrical member 36 having a diameter of approximately 4 mm or other suitable diameter. A series of cylindrical openings or channels 38 can be bored through this cylindrical member. Alternatively, a series of separate microtubules can be joined together by any well-known means such as adhesive and the like. An outer sleeve member 34 is provided which surrounds this plurality of microtubules 26. The syringe outlet 39 can have an opening of approximately 6 mm in diameter or any diameter large enough for the second plunger 24 to snuggly fit into the second syringe 22

Once the blood sample or buffy coat has been exposed to the treatment material or antigen, the second needle 30 may be attached adjacent to this opening 28 for re-injection into the individual. This design allows for a plurality of treatment agents and/or vaccine antigens to be simultaneously applied to an individual. This design also allows for the treatment of AIDS and other infectious disorders.

The invention has been described in such full, clear, concise, and exact terms so as to enable any person skilled in the art to which it pertains to make and use the same. It should be understood that variations, modifications, equivalents and substitutions for components of the specifically described embodiments of the invention may be made by those skilled in the art without departing from the spirit and scope of the invention as set forth in the appended claims. Persons who possess such skill will also recognize that the foregoing description is merely illustrative and not intended to limit any of the ensuing claims to any particular narrow interpretation.

I claim:

1. A system for medically treating/vaccinating an individual, said system comprising;
    (a) a first syringe for drawing a sample of blood from such individual, said first syringe comprising a first needle, a first plunger, and a tubular member extending between said first needle and said first plunger, said tubular member containing an anticoagulant;
    (b) centrifuge means for centrifuging said sample of blood contained within said first syringe to obtain a buffy coat and to enable one to express the packed red blood cell layer or plasma layer to position the buffy coat at an orifice of said first syringe;
    (c) a second syringe comprising a second plunger and at least one microtubule member containing one of a treatment agent and a vaccine antigen;
    (d) a pair of open ends formed within said at least one microtubule member and spaced apart from each other along a longitudinal axis thereof for drawing a portion of said buffy coat therein through said orifice of said first syringe and exposing said buffy coat to one of said treatment agent and vaccine antigen; and
    (e) a second needle capable of being attached onto one of said pair of said open ends of said at least one microtubule member for introducing said exposed sample into such individual to effect treatment/vaccination thereof.

2. A system for medically treating/vaccinating an individual as recited in claim 1 wherein at least one of said first plunger and said first needle are capable of being removed from said tubular member.

3. A system for medically treating/vaccinating an individual as recited in claim 2 including at least one cap for sealing said tubular member to enable said tubular member to be placed within said centrifuge means.

4. A system for medically treating/vaccinating an individual as recited in claim 1 wherein said first syringe includes means to expel red blood cells and/or a plasma layer from within said tubular member after subjecting said sample of blood to said centrifuge means.

5. A system for medically treating/vaccinating an individual as recited in claim 1 wherein said second plunger is capable of fitting loosely on said at least one microtubule to prevent an airlock on said at least one microtubule while drawing said buffy coat therein.

6. A system for medically treating/vaccinating an individual as recited in claim 5 wherein said buffy coat is drawn into said at least one microtubule by means of capillary action.

7. A system for medically treating/vaccinating an individual as recited in claim 1 wherein said second plunger is capable of being tightened to create an airlock to introduce said exposed sample into such individual.

8. A system for medically treating/vaccinating an individual as recited in claim 1 wherein said buffy coat is drawn into said at least one microtubule by means of syringe plunger pressure applied from said second plunger.

9. A system for medically treating/vaccinating an individual as recited in claim 1 wherein said at least one microtubule comprises a cylindrical member including a plurality of microtubules extending therethrough, each of said plurality of elongated microtubules having said pair of said open ends spaced from each other along said longitudinal axis of said each elongated microtubule and facilitating flow of one of said buffy coat and whole blood through said first and second open ends, said each elongated microtubule containing a different one of a plurality of one of said treatment agents and vaccine antigens.

10. A system for medically treating/vaccinating an individual as recited in claim 9 including an outer sleeve member surrounding said cylindrical member.

11. A system for medically treating an individual as recited in claim 9 wherein said plurality of one of treatment agents and vaccine antigens are capable of being simultaneously administered to such individual through said second needle.

12. A system for medically treating/vaccinating an individual as recited in claim 1 wherein said at least one microtubule comprises a plurality of separate microtubules joined together capable of being exposed to a plurality of one of said treatment agents and vaccine antigens.

13. A system for medically treating/vaccinating an individual as recited in claim 12 including an outer sleeve member surrounding said plurality of microtubules.

14. A system for medically treating an individual as recited in claim 12 wherein said plurality of one of treatment agents and vaccine antigens are capable of being simultaneously administered to such individual through said second needle.

15. A system for medically treating/vaccinating an individual, said system comprising;
    (a) a first syringe for drawing a sample of blood from such individual, said first syringe comprising a first needle, a first plunger, and a tubular member extending between said first needle and said first plunger, said tubular member containing an anticoagulant;

(b) centrifuge means for centrifuging said sample of blood contained within said first syringe to obtain a buffy coat and to enable one to express the packed red blood cell layer or plasma layer to position the buffy coat at an orifice of said first syringe;

(c) a second syringe comprising a second plunger and a plurality of elongated microtubule members, each containing a different one of a plurality of one of treatment agents and vaccine antigens;

(d) a pair of open ends provided within said each elongated microtubule member and opposing each other along a longitudinal axis thereof for drawing a portion of said sample of blood therein and exposing said sample of blood to said plurality of said different one of said treatment agents and vaccine antigens; and (e) a second needle capable of being attached onto one open end of said each elongated microtubule member for introducing said exposed sample into such individual to effect treatment/vaccination thereof.

16. A system for medically treating/vaccinating an individual, said system comprising;

(a) a first syringe for drawing a sample of blood from such individual, said first syringe comprising a first needle, a first plunger, and a tubular member extending between said first needle and said first plunger, said tubular member containing an anticoagulant;

(b) a centrifuge means for centrifuging said sample of blood contained within said first syringe to obtain a buffy coat and to enable one to express the packed red blood cell layer or plasma layer to position said buffy coat at an orifice of said first syringe;

(c) a plurality of elongated microtubules, each of said plurality of elongated microtubules having a first end opening and a second end opening spaced from said first end opening along a longitudinal axis of said each elongated microtubule and facilitating flow of said buffy coat through said first and second end openings, said each elongated microtubule containing a different one of a plurality of one of treatment materials and vaccine antigens, whereby said portion of said buffy coat is being drawn through said orifice of said first syringe and exposed to said different one of said plurality of one of treatment materials and vaccine antigens; and (e) a second needle capable of being attached onto said at least one open end of said at least one microtubule member for introducing said exposed sample into such individual to effect treatment/vaccination thereof.

* * * * *